US011151421B2

(12) United States Patent
Joyce et al.

(10) Patent No.: US 11,151,421 B2
(45) Date of Patent: Oct. 19, 2021

(54) METHOD FOR TREATING A SURFACE

(71) Applicant: The Procter & Gamble Company, Cincinnati, OH (US)

(72) Inventors: Jonathan Livingston Joyce, Independence, KY (US); Faiz Feisal Sherman, Mason, OH (US); Jennifer Theresa Werner, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/906,050

(22) Filed: Jun. 19, 2020

(65) Prior Publication Data
US 2020/0320350 A1 Oct. 8, 2020

Related U.S. Application Data

(63) Continuation of application No. 16/015,230, filed on Jun. 22, 2018, now Pat. No. 10,726,301.

(60) Provisional application No. 62/526,396, filed on Jun. 29, 2017.

(51) Int. Cl.
| | |
|---|---|
| *G06K 9/62* | (2006.01) |
| *A45D 44/00* | (2006.01) |
| *A61B 5/00* | (2006.01) |
| *G06K 9/46* | (2006.01) |
| *G06N 20/00* | (2019.01) |
| *G06Q 50/00* | (2012.01) |

(52) U.S. Cl.
CPC ......... *G06K 9/6262* (2013.01); *A45D 44/005* (2013.01); *A61B 5/44* (2013.01); *G06K 9/4628* (2013.01); *G06K 9/6218* (2013.01); *G06K 9/6267* (2013.01); *G06N 20/00* (2019.01); *G06Q 50/01* (2013.01); *A61B 5/0077* (2013.01); *A61B 5/441* (2013.01); *A61B 5/448* (2013.01); *A61B 5/7264* (2013.01); *A61B 5/7275* (2013.01); *A61B 5/74* (2013.01)

(58) Field of Classification Search
CPC .. G06K 9/6262; G06K 9/6267; G06K 9/4628; G06K 9/6218; A45D 44/005; A61B 5/44; A61B 5/441; A61B 5/74; A61B 5/7275; A61B 5/0077; A61B 5/7264; A61B 5/448; G06N 20/00; G06Q 50/01
See application file for complete search history.

(56) References Cited

U.S. PATENT DOCUMENTS

| | | |
|---|---|---|
| 8,582,878 B1 | 11/2013 | Tzur et al. |
| 2003/0065523 A1 | 4/2003 | Pruche |
| 2015/0057622 A1 | 2/2015 | Hyde |
| 2017/0231490 A1* | 8/2017 | Toth ........................ A61B 90/37 600/558 |
| 2018/0197624 A1* | 7/2018 | Robaina ................. G16H 80/00 |
| 2019/0005355 A1 | 1/2019 | Joyce |

FOREIGN PATENT DOCUMENTS

| | | |
|---|---|---|
| EP | 1297781 A1 | 4/2003 |
| WO | WO200969077 A2 | 6/2009 |
| WO | WO2009091409 A1 | 7/2009 |

OTHER PUBLICATIONS

International Search Report and Written Opinion dated Sep. 24, 2018, U.S. Appl. No. 16/015,230, 13 pgs.
Yoshitani et al., "LumiO: A Plaque-aware Toothbrush", Ubicomp '16, Sep. 12-16, 2016, Heidelberg Germany, pp. 605-615.
All Office Actions cited in U.S. Appl. No. 16/015,230.

* cited by examiner

*Primary Examiner* — Phuoc Tran
(74) *Attorney, Agent, or Firm* — Sarah M DeCristofaro; Steven Robert Chuey

(57) ABSTRACT

Method for treating a surface includes: automatically evaluating at least one digital image which includes the target surface; determining the nature of the target surface according to the evaluation of the at least one digital image; determining at least one available treatment implement according to the evaluation of the at least one image; determining the nature of the surface treatment according to the evaluation of the at least one image; automatically determining a use of the determined treatment implement in the determined treatment of the determined surface; and providing information analogous to the determined use of the treatment implement.

19 Claims, No Drawings

METHOD FOR TREATING A SURFACE

FIELD OF THE INVENTION

The invention relates to methods for treating or altering surfaces. The invention relates particularly to methods for evolving the treatment of a surface over time and repeated treatments of the surface.

BACKGROUND OF THE INVENTION

Consumers interact with surfaces through the use of consumer products. In some cases, consumers interact with particular surfaces repeatedly over the course of the useful life of the consumer goods and over the course of the life of the consumer themselves. Despite the repeated interactions and the accompanying familiarity with the surface and the interaction, there is typically room for improvement in the interaction in terms of how the consumer product is utilized and the resulting efficacy of the surface treatment accomplished via the interaction. What is needed is a method for evaluating the interaction or series of interactions which includes feedback to the consumer in terms of altering or modifying the details of the interaction in order to achieve a more efficacious interaction with and treatment of the targeted surface, enhance the treatment experience via gamification, as well as providing an overlay of information drawn from current treatment and fashion trends derived from social networks.

SUMMARY OF THE INVENTION

In one aspect, the method for treating a surface includes: automatically evaluating at least one digital image which includes the target surface; determining the nature of the target surface according to the evaluation of the at least one digital image; determining at least one available treatment implement according to the evaluation of the at least one image; determining the nature of the surface treatment according to the evaluation of the at least one image; automatically determining a use of the determined treatment implement in the determined treatment of the determined surface; and providing information analogous to the determined use of the treatment implement, or information intended to enhance the treatment activity by either distracting the user or making a game of the treatment regimen during the time the treatment is occurring.

DETAILED DESCRIPTION OF THE INVENTION

As used herein, the terms: machine learning, advanced machine learning, artificial intelligence, and deep learning refer to computational methods including the creation and interconnection of pluralities of simulated neurons in a mathematical model emulating the functioning of organic intelligence. The computational structures may include multiple layers of such simulated neurons where there are connections not only between neurons in a particular layer but also connections between layers as well as structures enabling the propagation of information from each layer forward to the next layer and also the backward propagation of information through the layers as the system undergoes training by exposure to data relevant to the task(s) the overall network is intended to undertake. The computational structures may include recurrent neural networks such as long-short-term memory (LSTM) and Gated Recurrence Unit (GRU) neural network structures. The output of the network may be taken from the final layer or from any intermediate layer depending upon the nature of the task and the overall structure of the network.

The systems and methods herein may include training one or more convolutional neural networks ("CNN") for determining the method of treating a surface. The CNN can be used to identify target surfaces, treatment implements and practitioner information relevant to the treatment method determined by the CNN. The CNN may utilize training images and/or audio data to train the convolutional neural network and may receive one or more training images or audio files to be utilized by the CNN to determine elements that define surface types, treatment implements, and practitioners. Once the CNN is trained, a user may capture an image (e.g., a digital image) of the target surface, implement, practitioner, for analysis by the CNN. The analysis of the captured image may include a determination of the target surface type, implement type, practitioner information as well as treatment method, additional relevant treatment products and treatment regimen information. The CNN and RNN structures may be used in sequence or in parallel to evaluate the data and determine a surface.

A system for practicing the methods of the invention may include a network, which may be embodied as a wide area network (such as a mobile telephone network, a public switched telephone network, a satellite network, the internet, etc.), a local area network (such as wireless-fidelity, Wi-Max, ZigBee™, Bluetooth™, etc), and/or other forms of networking capabilities. Coupled to the network are a computing device, a remote computing device, a kiosk computing device, and a training computing device.

The computing device may be a mobile telephone, a tablet, a laptop, a personal digital assistant, an instrumented or smart mirror, and/or other computing device configured for capturing, storing, and/or transferring images such as digital photographs and video. Accordingly, the mobile computing device may include an image capture device such as a digital camera, including depth sensing cameras and/or may be configured to receive images from other devices. The mobile computing device may include a memory component, which stores image capture logic and interface logic. The memory component may include random access memory (such as SRAM, DRAM, etc.), read only memory (ROM), registers, and/or other forms of computing storage hardware. The image capture logic and the interface logic may include software components, hardware circuitry, firmware, and/or other computing infrastructure, as described herein. As described in more detail below, the image capture logic may facilitate capturing, storing, preprocessing, analyzing, transferring, and/or performing other functions on a digital image of a user. The interface logic may be configured for providing one or more user interfaces to the user, which may include questions, options, and the like. The mobile computing device may also be configured for communicating with other computing devices via the network.

The remote computing device may also be coupled to the network and may be configured as a server (or plurality of servers), personal computer, mobile computer, and/or other computing device configured for creating and training a convolutional neural network for feature detection and treatment method determination. Features detected by the system may include edges, shapes, colors, which may be used to identify age, gender, skin type, hair type, floor type, fabric type, tooth color, skin color, pimples/acne, redness, shine of skin & hair. Products/Devices—toothbrushes, comb, hair brush, ProX, razors, grooming devices, Swiffer, beauty/ cosmetic device. Accordingly, the remote computing device may include a memory component, which stores training logic and analyzing logic. The training logic may facilitate creation and/or training of the CNN, and thus may facilitate creation of and/or operation of the convolutional neural network. The analyzing logic may cause the remote computing device to receive data from the mobile computing device (or other computing device) and process the received data for providing a treatment product recommendation, etc.

A training computing device may be coupled to the network 100 to facilitate training of the CNN. For example, a trainer may provide one or more images to the CNN via the training computing device. The trainer may also provide information and other instructions to inform the CNN which assessments are correct and which assessments are not correct. Based on the input from the trainer, the CNN may automatically adapt, as described in more detail below.

It should also be understood that while the remote computing device is described as performing the convolutional neural network processing, this is merely an example. RNNs or multi-layer-perceptron (MLP) may be used as alternative network architectures that and applied to video or other digital data including audio data. Any of these networks can be used since they are capable of analyzing video. The convolutional neural network processing may be performed by any suitable computing device, as desired.

The present system may include a convolutional neural network ("CNN") that functions as a surface treatment expert system. For example, a CNN may be stored as logic in the memory component of a computing device. The CNN may be configured to receive a training image (or a plurality of training images) and take raw image pixels from the training image as input and automatically learn feature extractors that are relevant for determining surface, implement, and practitioner types from a captured digital image. Recent advances in a machine learning technique called deep learning have resulted in breakthrough performance in the realm of neural networks, such as is described in U.S. Pat. No. 8,582,807. Deep-learning-type neural networks utilize a plurality of layers inspired by the human visual cortex.

The CNN may be trained using predefined features and/or auto-learned features. After the CNN is trained, it may be used to determine surface treatment options from a captured image of the user from the learned features. In some instances, the CNN can learn to identify important features in an image through a process called supervised learning. Supervised learning generally means that the CNN is trained by analyzing examples of images in which the surface treatment options have been pre-defined. Depending on the accuracy that is desired, the number of training images may vary from a few images to a continuous input of images to provide for continuous training. Regardless, after training, the CNN learns key features for predicting the treatment method accurately for a wide range of surface types.

The CNN may include a plurality of stages. A first stage may include preprocessing and a second stage may include convolutional neural network training. During preprocessing, one or more features common to most scenarios and users, ("anchor features"), in a received image may be detected. The detection may be made based on edge detection, shape detection, and/or similar detection mechanisms, as are known. Based on the location of the anchor feature(s), the images may be scaled and rotated to make the image substantially level and with the anchor feature(s) arranged in a predetermined position in the final image. By doing this, the training images may be consistently aligned, thus providing more consistent results. The image may then be cropped to a predetermined area of pixels as input for further processing.

During preprocessing, data augmentation may also be performed to create additional samples from the training images. For example, the input image may be randomly enlarged and/or shrunk, randomly rotated in a clockwise direction and/or in a counter clockwise direction, randomly cropped, and/or randomly changed with regard to saturation and/or exposure. In some instances, the input image may be subjected to random vertical dropout, which randomly drops out a column of pixels (feature map) of the image. The higher the layer, the more area of the element the dropout covers. By dropping out an entire column of pixels in the input image, the CNN may learn to rely on a variety of features for surface treatment evaluation, rather than one particular feature. Random vertical dropout may also prevent over training of the CNN, thus maintaining a desired accuracy level. Regardless of the techniques implemented, data augmentation allows the CNN to become more robust against variation in input images. This way, the CNN learns to extract important features under expected environmental variation caused by the way people take images, the conditions in which images are taken, and the hardware used to take images.

Preprocessing may also include normalization. As an example, global contrast normalization may be utilized to standardize the training images (and/or images of users). Similarly, the images may be masked with a fixed (or predetermined) size oval mask to minimize the influence of other features. This also forces the CNN to learn and not depend on only information in more fixed spatial location of the image.

During training, embodiments described herein may utilize mini-batch stochastic gradient descent (SGD) with Nesterov momentum (and/or other algorithms) to train the CNN. An example of utilizing a stochastic gradient descent is disclosed in U.S. Pat. No. 8,582,807. The objective function may include a mean square error. In some embodiments, about 10% of the training subject may be withheld. The training error and validation error on the withheld set may be monitored for training progress.

Once the CNN is trained, one or more of the CNN parameters may be fixed. As described in more detail below, a captured image may be forward propagated through the CNN to obtain a determined surface treatment regimen, which can optionally be displayed to the user, for example, on a mobile computing device.

The CNN may include an inputted image, one or more convolution layers $C_1$, $C_2$, one or more subsampling layers $S_1$ and $S_2$, a fully integrated layer, and an output. To begin an analysis or to train the CNN, an image is inputted into the CNN (e.g., the image of a user). The CNN may sample one or more portions of the image to create one or more feature maps in a first convolution layer $C_1$. For example, the CNN may sample six portions of the image to create six features maps in the first convolution layer $C_1$. Next, the CNN may subsample one or more portions of the feature map(s) in the first convolution layer $C_1$ to create a first subsampling layer $S_1$. In some instances, the subsampled portion of the feature map may be half the area of the feature map. For example, if a feature map comprises a sample area of 28×28 pixels from the image, the subsampled area may be 14×14 pixels. The CNN may perform one or more additional levels of sampling and subsampling to provide a second convolution layer $C_2$ and a second subsampling layer $S_2$. It is to be appreciated that the CNN may include any number of convolution layers and subsampling layers as desired. Upon completion of final subsampling layer, the CNN generates a fully connected layer $F_1$, in which every neuron is connected to every other neuron. From the fully connected layer $F_1$, the CNN can generate an output such as a predicted age or a heat map.

In some instances, at least some of the images and other data described herein may be stored as historical data for later use. As an example, tracking of user progress may be determined based on this historical data. Other analyses may also be performed on this historical data, depending on the embodiment.

In one embodiment, a CNN based model is used for detecting and tracking grooming implements in a consumer video. The model utilizes multiple CNNs and other neural network components (such as a fully-connected network, or an RNN) to accomplish this task. The consumer video is fed into the model as a series of image frames. Each image frame is first processed by a CNN to extract a set of feature maps (high-level features of the image). A second CNN, a Region Proposal Network, is used to propose a series of possible regions within the feature maps that might contain the grooming implement. The feature maps within the proposed regions are then extracted to be further proposed to a fully connected network to decide whether the proposed regions contain a grooming implement, refine the proposed regions positions, and map the coordinates of the proposed regions to the original image. The end result is that for each image frame, the model is able to decide whether a grooming implement exists, and if yes, the position of the grooming implement within the image. Concurrently, the consumer's face can also be located using various facial recognition algorithms including CNN or any other facial detector algorithm. It is possible to also have the face as part of the object detected in the described region proposal network. It is also possible to overlay a recurrent neural network to capture temporal information of the video. By combining location information of both grooming implement and consumer's face, the implement can respond accordingly to provide best grooming experience. In one embodiment, the operating parameters of the implement may be altered according to the manner in which the user is shaving, or otherwise grooming themselves or others. In one embodiment, the system may provide information to the user relating to the current as well as historic uses of the grooming implement and the target surface.

The image(s), as well as one or more outputs from the neural network may be passed to a database and aggregated with similar data from other users of the method. The aggregated data may be evaluated and categorized into clusters using known clustering methods. The instant user, surface and implement may then be associated with one or more of the now defined clustered populations based upon the data for the user, surface and implement. The association with particular cluster populations may then lead to the provision of cluster specific information to the user as part of the method. As an example, a user may be categorized according to age, ethnicity and gender and a comparison of the user's data with that of the cluster population for the same gender, age and ethnicity may provide insights of use to the practitioner when they are provided as part of the process.

In one aspect, a method for treating a target surface includes the steps of: automatically evaluating at least one digital image including the target surface. The digital image or collection of digital images, or digital video, of an interaction including the target surface may be provided to a machine learning system for evaluation. The collection of images may further include additional data associated with the content or context of the images. Data including audio, temperature, humidity or other environmental data captured contemporaneously with the images. The system may previously have been trained to identify the nature of the target surface by presenting the system with training data including images of representative target surfaces either in isolation or together with other data as indicated above. The nature of the target surface may include attributes including a categorization of the surface, such as skin, facial skin, teeth, fabrics, leather, plastics, wood, glass, ceramic, stone, or other hard or soft surfaces, as well as the current condition of the surface, the presence of facial hair, plaque, dirt, stains, and combinations thereof upon the target surface may be determined by the analysis of the surface via the images including the surface. The surface roughness or surface finish may also be determined.

The analysis of the at least one image may further identify or determine at least one available treatment implement. In one embodiment, the determination may comprise determining the presence of a hand-held treatment implement. In one embodiment, the determination may be made by matching content in the current images with images of suitable implements presented in the training data set. In one embodiment, the determination may be made by inference wherein particular implements are associated with certain surfaces according to previous definitions made available for the analysis. In this embodiment, a toothbrush may be associated with teeth, razors and implements with skin—body hair, scrub brushes with hard surfaces and so forth.

Further analysis of the at least one image and additional data may determine at least one surface treatment associated with the identified target surface in isolation or in conjunction with the identified treatment implement. This determination may be made utilizing the determination of the nature of the surface, the treatment implement, the practitioner, or combinations thereof. As an example, a grooming regimen may be determined as appropriate for a combination of a grooming implement and skin with hair. The analysis may then determine a use of the identified implement in the completion of the identified surface treatment.

Subsequent to the determinations, information analogous to the determined use may be provided to a user via a display system. Such information may include specific instructions regarding the handling and use of the implement in undertaking the treatment, the likely results of undertaking the treatment, the progression of the treatment as evaluated by the method over a series of treatments, the condition of the implement relative to performing the treatment and so forth. The information may be provided via digital display screen(s), by auditory cues from the implement or from distinct loudspeakers, or by visual cues such as indicator lights or other lighting changes in the treatment environment. In one embodiment, the step of providing information comprises providing cues analogous to the spatial interaction between the determined implement and the determined surface. In one embodiment, the step of providing information comprises providing information analogous to the temporal interaction of the determined implement and the determined surface. In one embodiment, the step of providing information comprises providing information through an alteration of a property of the determined implement.

In one embodiment, the information to be presented may be stored in a database and called in response to the output of the CNN. The presented information may be real-time information gathered during the treatment, information from the database and hybrid combinations of the two. As an example, a template display of upper and lower teeth may be presented to the user overlaid with real-time data illustrating which portions of the user's teeth have and have not been brushed during the current session. Data from the database illustrating trends of the user's brushing history may be presented.

In one embodiment, the step of providing information may include providing information associated with the determined use, product or implement as well as information associated with the user's social network. Social network information accessed using account information provided by the user may enable the presentation of information regarding similar treatments undertaken by members of the user's social network including similarities and differences between the treatment undertaken by the user and those treatments undertaken by other members of the user's social network. The social network information may also be used as an indicator of which social influencers are most likely to have an effect upon the user. This information may be used to select celebrity or social influencer how-to instructional content to present to the user as well as product review and testimonial information from the identified influencers or nearest analog to the identified influencers.

In one embodiment, the method further comprises the step of providing information regarding a treatment implement relevant to the determined surface or surface treatment, wherein the implement is not detected in the analysis of the data. As an example, analysis of the data may indicate the use of a grooming implement without the use of a complementary product which would improve or enhance the treatment activity. In this example, information regarding the missing product may be provided to the user.

In one embodiment, the step of providing information may include a gamification aspect. The information to be provided may be presented in the form of a game for the user. The game may include aspects such as point scoring, competition with others, and rules of play. As an example, use of an oral care implement such as a toothbrush may involve the presentation of the information related to the time spent brushing and the areas of the oral cavity I, including dental surfaces, tongue and gums, treated thus far as well as remaining to be treated, may be presented in the form of a game wherein the user must move the implement in a manner to clear objects from the display as a timer counts up or down. In this embodiment, the graphic elements presented for removal may coincide with the surfaces to be cleansed and may be removed from the display only after sufficient time has been spent by the user in treating/cleaning those surfaces.

In one embodiment, the method may further comprise the step of determining one or more properties of a treatment practitioner according to the evaluation of the at least one image. Properties including the practitioner gender, dominant hand, skin condition, beard condition, may be determined by analyzing the data and the context of the data together with other information regarding the user and the environment of the use. The determined properties of the practitioner may be used as inputs in determining what information to provide as the treatment activity is evaluated. Information specifically applicable to the user's gender, dominant hand, skin condition, beard condition, and combinations thereof may be provided.

In one embodiment, the information about the user may be combined with information about the product including brand, package quantity and quantity used for each treatment, to calculate product quantity remaining and thereby provide the user with an indication of when the current product is likely to run out as well as an indication of when the product should be replaced or re-ordered using the user's typical means of acquiring the product.

In one embodiment, the method further comprises the step of determining one or more environmental properties according to the evaluation of the one or more images together with at least one additional data source. As an example, the method may determine the location of the practitioner and the surface, the time of day, the lighting available at the location and other features of the local or external environment. The determined environmental properties may be used as input in determining what information to provide to the user as part of the method.

In one embodiment, the method may further comprise steps of: tracking an initial determined treatment of a determined target surface; providing information analogous to the determined treatment, tracking and evaluating subsequent treatments of the target surface; and altering subsequent provided information according to a machine learning evaluation of the tracked initial and subsequent determined treatments and previously provided information. As an example, a user may use the method to evaluate their shaving experience. Information may be provided to the use to enhance their shaving experience. Subsequent evaluations may indicate that portions of the previously provided information have been successfully followed or included in the shaving activity while other portions have not yet been added successfully. Subsequent to this determination, the provided information may be tailored to include only that information related to the portions which have not yet successfully been added to the treatment activity—in this example, shaving. Information types include shaving or treatment trends, ongoing treatment results—how well the user is shaving, what opportunities remain to improve their experience, and diagnostic information relating to the user's grooming implement as well as their shaving activities.

In one embodiment, the method may further comprise steps of: tracking an initial determined treatment of a determined target surface; tracking at least one subsequent determined treatment of the same determined treatment surface; using machine learning in evaluating the combination of tracked determined treatments of the determined target surface; and providing information analogous to the determined treatment of the determined target surface according to the evaluation of the combination of tracked determined treatments. The information provided may include indications of improvements to the grooming activities as well as outstanding opportunities for further improvements based upon a progression in the grooming results.

In this embodiment, the step of: machine learning in evaluating the combination of tracked determined treatments of the determined target surface, may comprise evaluating the practitioner in the combination using the environmental context of the treatment together with any information provided by the user.

In this embodiment, the step of: machine learning in evaluating the combination of tracked determined treatments of the determined target surface, may comprise evaluating the implement in the combination, the implement may be evaluated in terms of the manufacturer and model of the implement as well as the operational condition of the implement considered in terms of the implement's performance in completing the surface treatment. As an example, as the operating condition of the implement declines, the work necessary to complete the task will change.

In this embodiment, the step of: machine learning in evaluating the combination of tracked determined treatments of the determined target surface, may comprise evaluating the surface in the combination. The nature of the surface may be evaluated to provide an input to the determination of the information to be provided. Evaluation of a user's face may indicate a light or heavy growth of hair leading to the provision of different information dependent upon the facial hair present at the time of treatment.

In one embodiment, the method further comprises the step of altering a performance characteristic of the implement. In this embodiment, the driven frequency of the implement may be changed to alter the performance or to provide an auditory cue to the practitioner regarding the treatment of the surface using the implement.

The methods of the invention may be practiced using a remote computing device, according to embodiments described herein. The remote computing device may include a processor, input/output hardware, network interface hardware, a data storage component (which stores image data, product data, and/or other data), and a memory component. The memory component, may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the remote computing device and/or external to the remote computing device.

The memory component may store operating logic, the training logic and the analyzing logic. The training logic and the analyzing logic may each include a plurality of different pieces of logic, each of which may be embodied as a computer program, firmware, and/or hardware, as an example. The system may also include a local communications interface which may be implemented as a bus or other communication interface to facilitate communication among the components of the remote computing device.

The processor may include any processing component operable to receive and execute instructions (such as from a data storage component and/or the memory component. As described above, the input/output hardware may include and/or be configured to interface with the components.

The network interface hardware may include and/or be configured for communicating with any wired or wireless networking hardware, including an antenna, a modem, a LAN port, wireless fidelity (Wi-Fi) card, WiMax card, Bluetooth™ module, mobile communications hardware, and/or other hardware for communicating with other networks and/or devices. From this connection, communication may be facilitated between the remote computing device and other computing devices. The communication capability may also extend to communication with particular treatment implements, such implements also comprising communications elements as described above, for the purpose of determining and/or altering operational parameters of the implements.

The operating system logic may include an operating system and/or other software for managing components of the remote computing device. As discussed above, the training logic may reside in the memory component and may be configured to cause the processor to train the convolutional neural network. Similarly, the analyzing logic may be utilized to analyze images for skin age prediction.

It should be understood that while the components described here are set forth as residing within the remote computing device, this is merely an example. In some embodiments, one or more of the components may reside external to the remote computing device and/or the remote computing device may be configured as a mobile device. It should also be understood that, while the remote computing device is illustrated as a single device, this is also merely an example. In some embodiments, the training logic and the analyzing logic may reside on different computing devices. As an example, one or more of the functionalities and/or components described herein may be provided by the mobile computing device and/or other devices, which may be communicatively coupled to the remote computing device. These computing devices may also include hardware and/or software for performing the functionality described herein.

Additionally, while the remote computing device is described with the training logic and the analyzing logic as separate logical components, this is also an example. In some embodiments, a single piece of logic may cause the remote computing device to provide the described functionality.

The methods described may be implemented using computer systems built around central processing units, graphic processing units, field-programmable gate arrays, tensor processing units, deep learning accelerators, and combinations thereof. The methods may be programmed using one or more deep-learning libraries including Tensorflow, Tensorflow Lite, Torch, pyTorch, Caffe, Caffe2, Mxnet, Theano, and combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for treating a target surface, the method comprising steps of:
  a. using machine learning in evaluating audio data and at least one digital image;
  b. determining a practitioner according to the evaluation of the audio data;

c. determining an interaction between an implement and a target surface according to the evaluation of the at least one digital image;
d. using machine learning to determine a use of the determined implement in the determined treatment of the determined surface;
e. altering performance characteristics of the implement or providing information analogous to the determined use.

2. The method of claim 1, comprising using machine learning in evaluating at least one digital image to determine the interaction between implement and a practitioner.

3. The method of claim 1, wherein step d. also includes using machine learning in evaluating at least one digital image to determine the interaction between a practitioner and target surface.

4. The method of claim 1, wherein the step of determining the nature of the target surface comprises determining one or more properties of the surface associated with surface treatments.

5. The method of claim 1, wherein the step of determining at least one available treatment implements comprises determining the presence of a hand-held surface treatment implement.

6. The method of claim 1, wherein the step of determining the nature of the surface treatment comprises evaluating the nature of the determined surface and the nature of the determined implement.

7. The method of claim 1, wherein the step of determining the nature of the surface treatment comprises using machine learning in evaluating at least one of: the nature of the surface, the implement, and the practitioner.

8. The method of claim 1, wherein the step of providing information comprises providing cues analogous to the spatial interaction between the determined implement and the determined surface.

9. The method of claim 1, wherein the step of providing information comprises providing information analogous to the temporal interaction of the determined implement and the determined surface.

10. The method of claim 1, wherein the step of providing information comprises providing information through an alteration of a property of the determined implement.

11. The method of claim 1, comprising the steps of:
a. tracking an initial determined treatment of a determined target surface;
b. evaluating the initial determined treatment according to the provided information; and
c. altering the provided information according to a machine learning evaluation of the tracked initial determined treatment.

12. The method of claim 1, comprising the steps of:
a. tracking an initial determined treatment of a determined target surface;
b. tracking at least one subsequent determined treatment of the same determined treatment surface;
c. using machine learning in evaluating the combination of tracked determined treatments of the determined target surface; and
d. providing information analogous to the determined treatment of the determined target surface according to the evaluation of the combination of tracked determined treatments.

13. The method of claim 12, wherein the step of machine learning in evaluating the combination of tracked determined treatments of the determined target surface comprises evaluating the practitioner in the combination.

14. The method of claim 12, wherein the step of machine learning in evaluating the combination of tracked determined treatments of the determined target surface comprises evaluating the implement in the combination.

15. The method of claim 12, wherein the step of machine learning in evaluating the combination of tracked determined treatments of the determined target surface comprises evaluating the surface in the combination.

16. A method for treating a target surface, the method comprising steps of:
a. evaluating at least one digital image including the target surface using machine learning;
b. determining the nature of the target surface according to the evaluation of the at least one image;
c. evaluating at least one audio data using machine learning;
d. determining at least one available treatment implement according to the evaluation of the audio data;
e. altering performance characteristics of the implement or providing information analogous to the determined use.

17. The method according to claim 16, comprising using machine learning in evaluating at least one audio data of the environment to determine a practitioner.

18. The method of claim 16, comprising using machine learning in evaluating at least one image to determine the interaction between implement and practitioner.

19. The method of claim 16, comprising using machine learning in evaluating at least one image to determine the interaction between practitioner and target surface.

* * * * *